(12) United States Patent
Kawamuki (10) Patent No.: US 9,523,641 B2
(45) Date of Patent: Dec. 20, 2016

(54) FLUORESCENCE DETECTION DEVICE

(71) Applicant: Sharp Kabushiki Kaisha, Osaka-shi, Osaka (JP)

(72) Inventor: Ryohhei Kawamuki, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 62 days.

(21) Appl. No.: 14/405,491

(22) PCT Filed: Jun. 11, 2013

(86) PCT No.: PCT/JP2013/066096
§ 371 (c)(1),
(2) Date: Dec. 4, 2014

(87) PCT Pub. No.: WO2013/191040
PCT Pub. Date: Dec. 27, 2013

(65) Prior Publication Data
US 2015/0153281 A1    Jun. 4, 2015

(30) Foreign Application Priority Data

Jun. 19, 2012 (JP) .................. 2012-137988

(51) Int. Cl.
*G01N 21/64* (2006.01)
*G01N 27/44* (2006.01)
*G01N 27/447* (2006.01)

(52) U.S. Cl.
CPC ...... *G01N 21/6456* (2013.01); *G01N 21/6486* (2013.01); *G01N 27/44721* (2013.01); *G01N 27/44778* (2013.01); *G01N 2021/6478* (2013.01); *G01N 2201/06113* (2013.01); *G01N 2201/101* (2013.01); *G01N 2201/104* (2013.01)

(58) Field of Classification Search
CPC ............ G01N 21/6456; G01N 21/6486; G01N 27/44721; G01N 27/44778; G01N 2201/101; G01N 2201/104
USPC ............................................... 250/458.1, 234
See application file for complete search history.

(56) References Cited

U.S. PATENT DOCUMENTS 3,952,372 A * 4/1976 Howell, Jr. ............... D01H 5/36
 19/238
4,130,253 A * 12/1978 Yasumatsu .............. B60R 22/34
 242/378.1
5,100,529 A * 3/1992 Fujii ................ G01N 27/44721
 204/612

(Continued)

FOREIGN PATENT DOCUMENTS

JP   2001-074656 A   3/2001

*Primary Examiner* — David Porta
*Assistant Examiner* — Blake Riddick
(74) *Attorney, Agent, or Firm* — Keating & Bennett, LLP (57) ABSTRACT

A scanning module (9) is disposed over a first plate (32). A first motor (39) of moving the scanning module (9) in a second scanning direction and a second motor (49) of moving the scanning module (9) in a first scanning direction are disposed under the first plate (32). In this manner, the first motor (39) and the second motor (49) being a heat source are disposed on a side opposite to a scanning module (9) side using the first plate (32) as a boundary, and thus a transferred amount of heat from the first motor (39) and the second motor (49) to the scanning module (9) decreases. As a result, accuracy of fluorescence detection is prevented from degrading due to thermal distortion of a detection optical system in the scanning module (9).

5 Claims, 7 Drawing Sheets

(56) References Cited

U.S. PATENT DOCUMENTS

| | | | | |
|---|---|---|---|---|
| 5,181,715 A * | 1/1993 | Ohkoda | ............ | B65H 5/00 271/272 |
| 5,229,074 A * | 7/1993 | Heath | ............ | G01N 35/1004 422/64 |
| 5,459,325 A * | 10/1995 | Hueton | ............ | G01N 21/6452 204/452 |
| 5,483,075 A * | 1/1996 | Smith | ............ | G01N 27/44782 204/461 |
| 5,587,796 A * | 12/1996 | Rakitsch | ............ | B41F 33/0036 356/425 |
| 5,670,375 A * | 9/1997 | Seaton | ............ | G01N 21/276 422/561 |
| 5,780,857 A * | 7/1998 | Harju | ............ | G01N 21/5911 250/458.1 |
| 5,853,666 A * | 12/1998 | Seaton | ............ | G01N 35/00029 356/246 |
| 5,900,640 A * | 5/1999 | Ogura | ............ | G01N 21/6456 250/583 |
| 6,024,920 A * | 2/2000 | Cunanan | ............ | G01N 21/253 356/432 |
| 6,043,880 A * | 3/2000 | Andrews | ............ | G01N 21/64 250/361 C |
| 6,172,360 B1 * | 1/2001 | Khovaylo | ............ | H04N 1/00519 250/208.1 |
| 6,762,840 B1 | 7/2004 | Kimura | | |
| 9,285,321 B2 * | 3/2016 | Kawamuki | ............ | G01N 21/6456 |
| 2001/0046712 A1 * | 11/2001 | Hang | ............ | G01N 21/6452 436/172 |
| 2004/0178334 A1 * | 9/2004 | Sasaki | ............ | G02B 21/002 250/234 |
| 2006/0000962 A1 * | 1/2006 | Imabayashi | ............ | G02B 21/245 250/201.2 |
| 2007/0051903 A1 * | 3/2007 | Chen | ............ | G01N 21/6428 250/458.1 |
| 2009/0147822 A1 * | 6/2009 | Tokhtuev | ............ | G01N 21/0332 374/142 |
| 2010/0002742 A1 * | 1/2010 | Basu | ............ | F28D 15/00 372/67 |
| 2010/0206102 A1 * | 8/2010 | Aso | ............ | F16C 29/082 74/89.4 |
| 2010/0270123 A1 * | 10/2010 | Ishino | ............ | B65G 17/066 198/465.1 |

* cited by examiner

FLUORESCENCE DETECTION DEVICE

TECHNICAL FIELD

The present invention relates to a fluorescence detection device.

BACKGROUND ART

Hitherto, a fluorescence detection system in which a fluorochrome is used as a marker has been used broadly in biochemistry or molecular biology. By using the fluorescence detection system, gene arrangement, gene mutation polymorphism analysis, protein separation and identification, or the like can be evaluated and the system is used in development of medicine and the like.

As an evaluation method using the fluorescent marker described above, a method is frequently used in which biological compounds including protein or the like are distributed in gel by electrophoresis and the distribution of the biological compounds is obtained by using fluorescence detection. In the electrophoresis, electrodes are disposed in a solution such as a buffer solution, and a direct current flows through the electrodes to generate an electric field gradient in the solution. At this time, when there is protein, Deoxyribonucleic acid (DNA), or ribonucleic acid (RNA) with electric charges in the solution, biomolecules can be separated in such a manner that molecules with plus charges are drawn to a negative terminal, and molecules with minus charges are drawn to a positive terminal.

Two-dimensional electrophoresis as an example of the evaluation method using the electrophoresis is an evaluation method in which biomolecules in a gel are two-dimensionally distributed by combining two types of electrophoresis methods. This method is considered as the most efficient method for proteome analysis.

As a combination of the electrophoresis, for example, two methods are mainly used: "isoelectric focusing using a difference between isoelectric points of pieces of protein" in a first dimension and "SDS-PAGE (sodium dodecyl sulfate-polyacrylamide gel electrophoresis) performing separation by a molecular weight of protein" in a second dimension. Fluorochromes are given to the protein as the biomolecules separated in this manner before or after electrophoresis.

An image reading device has come into wide use in biochemistry or molecular biology, and in the image reading device, excitation light is applied to a gel support in which the biomolecules (protein) produced in the above-described manner are two-dimensionally distributed, intensity of generated fluorescence is obtained, and a fluorescence distribution (protein distribution) image is displayed based on the obtained fluorescence intensity.

As a method of holding the two-dimensional distribution of the biomolecules, a method is also performed in which the protein is separated in the gel, and then the separated protein is transferred from the gel to a membrane by using electrophoresis or capillary phenomenon, in addition to holding of the distribution in the gel. In that case, an image reading device can image fluorescence distribution on a transfer support which is the membrane, similarly to a case of reading an image by using the gel support.

Japanese Unexamined Patent Application Publication No. 2001-74656 (PTL 1) discloses an image information reading device as the above-described image reading device which reads a biomolecule distribution image from the gel support or transfer support as described above in which the biomolecules are two-dimensionally distributed.

The image information reading device is an optical head scanning type of image information reading device. When the image information reading device irradiates a sample with excitation light and guides fluorescence emitted from the sample to detection means by an optical head, scanning means causes the optical head to move at a constant velocity with respect to the sample.

If described in detail, a hole mirror having a hole in the center thereof is mounted on the optical head which moves in a main scanning direction. Organism-derived biomaterials marked by fluorochrome are distributed in a scanning target. Laser beam (excitation light) having a wavelength at which the fluorochrome is excited, emitted from a laser light source, is reflected upwardly from a planar mirror. The reflected laser beam passes through the small hole of the hole mirror, and then the laser beam is concentrated at an objective lens and applied to the scanning target. The fluorochrome in the scanning target is excited to emit fluorescence. The fluorescence is reflected around the small hole of the hole mirror. A photo multiplier performs photoelectric conversion of the fluorescence and the converted fluorescence is detected. In this manner, the detected fluorescence is read as a corresponding image signal. Hereinafter, it is assumed that the above-described operation is repeated while the optical head is moved in a sub-scanning direction orthogonal to the main scanning direction, and thus a two-dimensional visible image (fluorescence image) is obtained.

A surface plate is disposed and fixed on a lower side of a sample stand. The laser light source and the photo multiplier are mounted on a lower surface of the surface plate. The optical head, a driving device for moving the optical head in the main scanning direction, and a driving device for moving the optical head in the sub-scanning direction are mounted on an upper surface of the surface plate.

However, the image information reading device in the related art has a problem as described below.

That is, the laser light source and the photo multiplier are mounted on the lower surface of the surface plate, and the optical head, the driving device for moving the optical head in the main scanning direction of the optical head, and the driving device for moving the optical head in the sub-scanning direction are mounted on the upper surface of the surface plate. The laser beam from the laser light source is reflected from two mirrors and is incident to the optical head which is mounted on the upper surface of the surface plate and moves in a two-dimensional direction. The fluorescence from the optical head is reflected from three mirrors and is incident to the photo multiplier which is mounted on the lower surface of the surface plate.

Accordingly, high-sensitivity is expected, however, an optical path of the laser beam from the laser light source to the scanning target and an optical path of the fluorescence from the scanning target to the photo multiplier are long. If the entirety of the image information reading device expands thermally, an extension ratio of the optical paths increases. A position relationship of optical members such as a lens and a mirror is shifted from a designed value, and thus there is a problem in that optical characteristics are degraded.

The various lenses and mirrors being the optical members and a motor of the driving device being a heat source are put on both sides of the surface plate. Accordingly, there is a problem in that the optical members are easily affected by a change in temperature of the atmosphere due to the heat source. As the rotation number of the motor becomes large so as for the optical head to perform scanning at a high speed, the more the optical members are further affected.

CITATION LIST

Patent Literature

PTL 1: Japanese Unexamined Patent Application Publication No. 2001-74656

SUMMARY OF INVENTION

Technical Problem

An object of the invention is to provide a fluorescence detection device in which optical members are unlikely to be affected by an increase of the temperature even though the temperature in the device increases due to generation of heat in a driving device of an optical head and peripheral circuits thereof.

Solution to Problem

To solve the problem, a fluorescence detection device according to the invention includes: a reference stand which has a plate shape and an opening; a scanning module that includes a light source which emits excitation light for excitation of fluorescence and a detection optical system which detects fluorescence emitted from a detection target based on the irradiation of the excitation light, and scans two-dimensionally in a first scanning direction and a second scanning direction substantially orthogonal to the first scanning direction; an upper operation support section which supports the scanning module to allow the scanning module to perform a reciprocating operation in the second scanning direction and in a plane direction of the reference stand; and a lower operation support section which is disposed on the reference stand and supports the upper operation support section to allow the upper operation support section to perform a reciprocating operation in the first scanning direction and in a plane direction of the reference stand. The upper operation support section includes a belt of causing the scanning module to perform a reciprocating operation in the second scanning direction; a belt driving section which drives the belt; and a belt pulling-down section which causes the belt to pass through the opening of the reference stand and to be pulled down from a scanning module side to a side opposite to the scanning module side. The belt driving section is positioned on the side opposite to the scanning module with respect to a surface of the reference stand and disposed in the belt pulling-down section.

According to the configuration, the belt driving section being a heat source is positioned on a side opposite to the scanning module with respect to a surface of the reference stand, and thus it is possible to prevent heat from the belt driving section from being transferred to the scanning module in the reference stand. Accordingly, a detection optical system of the scanning module is unlikely to be thermally affected.

An opening is formed in the reference stand so that the belt is pulled down toward a side opposite to a scanning module side and a belt pulling-down section where the belt driving section is disposed may pass through the reference stand when the scanning module performs scanning. Accordingly, it is possible to achieve both: that the belt driving section causes the scanning module to perform a reciprocating operation in the second scanning direction and that the belt driving section and the scanning module are disposed on opposite sides with respect to the reference stand.

Furthermore, the reference stand is configured to have high rigidity and mass such that the reference stand has stability in vibration or impact as well as heat. Thus, the upper operation support section is directly disposed on the stable reference stand or is indirectly disposed on the reference stand through another member, and the upper operation support section has a stable structure from the vibration of the belt driving section.

Furthermore, because the belt driving section is disposed on a side opposite to the scanning module with respect to the reference stand, it is unnecessary to provide a space for disposition of the belt driving section on a scanning module side of the reference stand and it is possible to reduce the height from the reference stand to the scanning module. Accordingly, it is possible to achieve high stability in operating of the scanning module and reduced size of the entirety of the fluorescence detection device.

In the fluorescence detection device according to an embodiment, the upper operation support section includes belt holding portions which hold a relative position between the belt and the belt driving section to be a predefined position. The upper operation support section is able to perform the reciprocating operation in the first scanning direction in a state where the relative position between the belt and the belt driving section is held to be the predefined position by the belt holding portions.

According to this embodiment, the entirety of the upper operation support section is formed integrally and the upper operation support section is supported by the lower operation support section so as to perform a reciprocating operation in the first scanning direction. Accordingly, movement in the first scanning direction and movement in the second scanning direction are not affected by each other and are completely independent from each other, and thus the scanning module easily performs the two-dimensional scanning.

In the fluorescence detection device according to another embodiment, the opening of the reference stand is long in the first scanning direction.

It is necessary to reduce an area of the opening of the reference stand as much as possible so as to reduce the quantity of heat transferred from the belt driving section to the scanning module. The belt is operated when the upper operation support section causes the scanning module to perform a reciprocating operation in the second scanning direction, but a position of the belt pulling-down section passing through the opening of the reference stand is not changed. When the scanning module is caused to perform a reciprocating operation in the first scanning direction, the entirety of the upper operation support section integrally moves in the first scanning direction, and thus the belt pulling-down section also moves in the first scanning direction.

According to this embodiment, the opening of the reference stand is long in the first scanning direction, and thus it is possible to reduce the area of the opening to the minimum in a range of not preventing the belt pulling-down section from moving.

In the fluorescence detection device according to another embodiment, the lower operation support section includes guide members which guide the upper operation support section in the first scanning direction and driving sections driving the entirety of the upper operation support section in the first scanning direction, and the driving sections are positioned on the side opposite to the scanning module with respect to the surface of the reference stand and are disposed to transfer a driving force to the belt pulling-down section.

According to this embodiment, not only the belt driving section of the upper operation support section but also the driving section of the lower operation support section, the driving section being a heat source, is positioned on the side opposite to the scanning module with respect to the reference stand. Accordingly, it is possible to prevent heat from the belt driving section and the driving section as a heat source from being transferred to the scanning module.

At that time, because a driving force in the driving section is transferred to the belt pulling-down section passing through the opening of the reference stand, it is possible to transfer the driving force in the driving section to the upper operation support section positioned on the side opposite to the driving section with respect to the reference stand.

The fluorescence detection device according to another embodiment includes covers which cover the opening of the reference stand such that the belt and the belt pulling-down section are movable when the scanning module performs two-dimensional scanning.

According to this embodiment, the cover covers the opening of the reference stand so as not to interfere in the belt and the belt pulling-down section. Accordingly, it is possible to further reduce the area of the opening of the reference stand and to further effectively block the heat from the heat source.

In the fluorescence detection device according to another embodiment, the detection target is loaded on a light transmissive sample stand. The scanning module is disposed to face a side of the sample stand opposite to a side of the sample stand on which the detection target is loaded. The scanning module detects fluorescence emitted from the detection target through the sample stand while performing the two-dimensional scanning along the sample stand.

According to this embodiment, it is possible to provide a fluorescence detection device able to detect fluorescence information in the detection target with two-dimensions and high accuracy while being unlikely to be thermally affected by the heat source such as the belt driving section.

Advantageous Effects of Invention

As is apparent, the fluorescence detection device of the invention causes the scanning module to perform two-dimensional scanning in the first scanning direction and the second scanning direction substantially orthogonal to the first scanning direction. The scanning module includes a light source which emits excitation light and a detection optical system which detects fluorescence emitted from a detection target based on the irradiation of the excitation light. Accordingly, lengths of two optical paths, an optical path of the excitation light from the light source to the detection target and an optical path from the detection target to the detection optical system, become short. The lengths of the optical paths are not changed when two-dimensional scanning is performed. As a result, even though the entirety of the fluorescence detection device expands, a ratio of extension of the optical paths become small, and it is possible to prevent degradation of the optical characteristics in the detection optical system.

Additionally, because the belt driving section being the heat source is positioned on the side opposite to the scanning module with respect to a surface of the reference stand, it is possible to prevent the heat from the belt driving section from being transferred to the scanning module in the reference stand. Accordingly, the detection optical system of the scanning module is unlikely to be thermally affected.

Furthermore, the reference stand is configured to have high rigidity and mass such that the reference stand has stability in vibration or impact as well as heat. Thus, the upper operation support section directly disposed on the stable reference stand or indirectly disposed on the reference stand through another member has a structure stable to the vibration of the belt driving section.

Furthermore, because the belt driving section is disposed on a side opposite to the scanning module with respect to the reference stand, it is unnecessary to provide a space for disposition of the belt driving section on a scanning module side of the reference stand and it is possible to reduce the height from the reference stand to the scanning module. Accordingly, it is possible to achieve high stability in operating of the scanning module and reduced size of the entirety of the fluorescence detection device.

DESCRIPTION OF EMBODIMENTS

Hereinafter, the invention will be described in detail with embodiments according to the invention.

Figure 1:
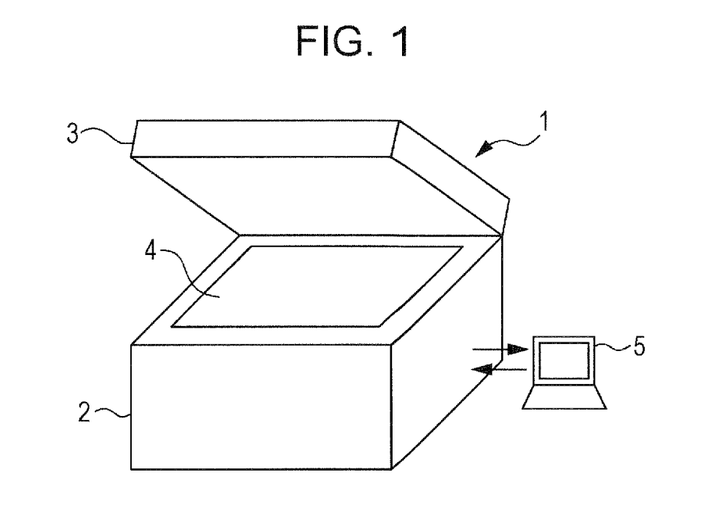
FIG. 1 is an appearance view of a fluorescence detection device according to the invention.

FIG. 1 is an appearance view of a fluorescence detection device according to an embodiment. The fluorescence detection device 1 is schematically configured by a main body 2 forming a housing and a lid 3 covering an upper surface of the main body 2. A sample stand 4 formed of glass is disposed on the upper surface of the main body 2. A gel support or a transfer support such as a membrane (not illustrated together) is set on the sample stand 4 as a sample (measurement target). Organism-derived biomaterials marked by, for example, a fluorescence material are distributed on the gel support or the transfer support.

An optical system is disposed under the sample stand 4. An excitation optical system irradiates a sample set on the sample stand 4 with excitation light from the lower part of the main body 2 through the sample stand 4. A detection optical system detects fluorescence which is emitted from the sample and transmitted by the sample stand 4. The detection optical system is coupled with an external terminal such as a Personal computer (PC) 5 and performs control of a measurement condition, and the like from the PC 5. The PC 5 creates a fluorescence image of the sample based on detection data and displays the created fluorescence image and the like on a built-in display screen.

Figure 2:
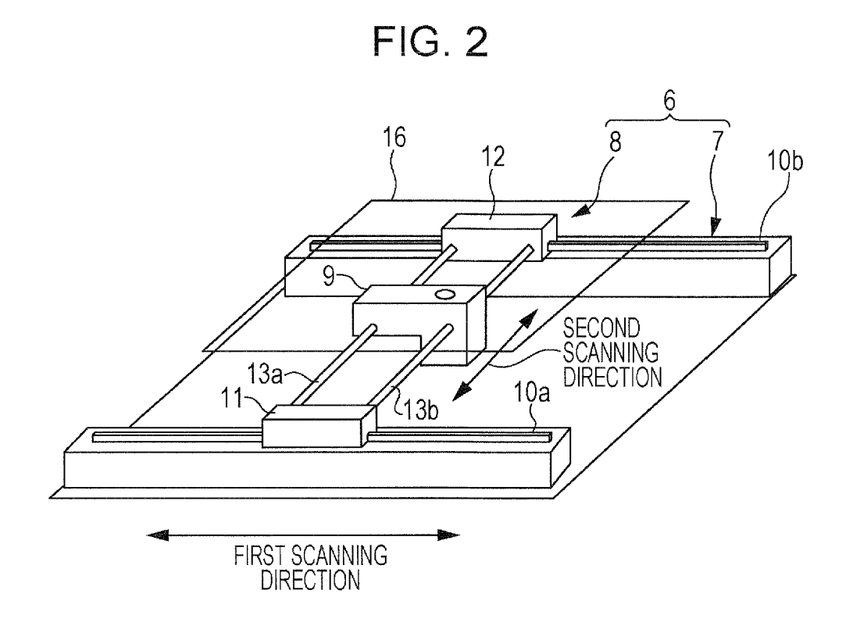
FIG. 2 is an appearance view of a scanning stage disposed under a sample stand in FIG. 1.

FIG. 2 is an appearance view of a scanning stage 6 disposed under the sample stand 4. The scanning stage 6 is configured by a first stage 7 being a reference and a second stage 8 placed on the first stage 7. A scanning module 9 is placed on the second stage 8. The detection optical system detecting the fluorescence is stored in the scanning module 9.

Two guide rails 10a and 10b are arranged on the first stage 7 constituting the scanning stage 6. The two guide rails 10a and 10b extend in a first scanning direction and face each other with a constant distance. The second stage 8 includes a first guide member 11 and a second guide member 12. The first guide member 11 is guided by the guide rail 10a of the first stage 7 and performs reciprocating motion in the first scanning direction. The second guide member 12 is guided by the guide rail 10b and performs reciprocating motion in the first scanning direction.

Two guide shafts 13a and 13b are arranged between the first guide member 11 and the second guide member 12 constituting the second stage 8. The two guide shafts 13a and 13b extend in a second scanning direction orthogonal to the first scanning direction and face each other with a constant distance. Holes for inserting the guide shafts 13a and 13b are formed in the scanning module 9. The scanning module 9 is guided by the guide shafts 13a and 13b and performs reciprocating motion in the second scanning direction.

A scanning method performed by the scanning stage 6 having the above-described configuration includes the following: first, the first guide member 11 and the second guide member 12 of the second stage 8 are guided by the guide rails 10a and 10b and move in the first scanning direction. The first guide member 11 and the second guide member 12 are positioned in the second stage 8 with respect to the first stage 7. After that, the scanning module 9 is guided by the guide shafts 13a and 13b and moves in the second scanning direction. The scanning module 9 is positioned with respect to the second stage 8. Then, two-dimensional scanning is performed on a sample 16 by repeating these operations.

Detailed description will be made later, but a scanning device is disposed under the scanning stage 6 in a lower portion of the sample stand 4 of the main body 2 constituting the housing so as to move the first and the second guide members 11 and 12 of the second stage 8 in the first scanning direction and to move the scanning module 9 in the second scanning direction. The scanning device includes a motor, a timing belt, a ball screw, a gear, a control board, a power source, wiring, and the like.

Figure 3:
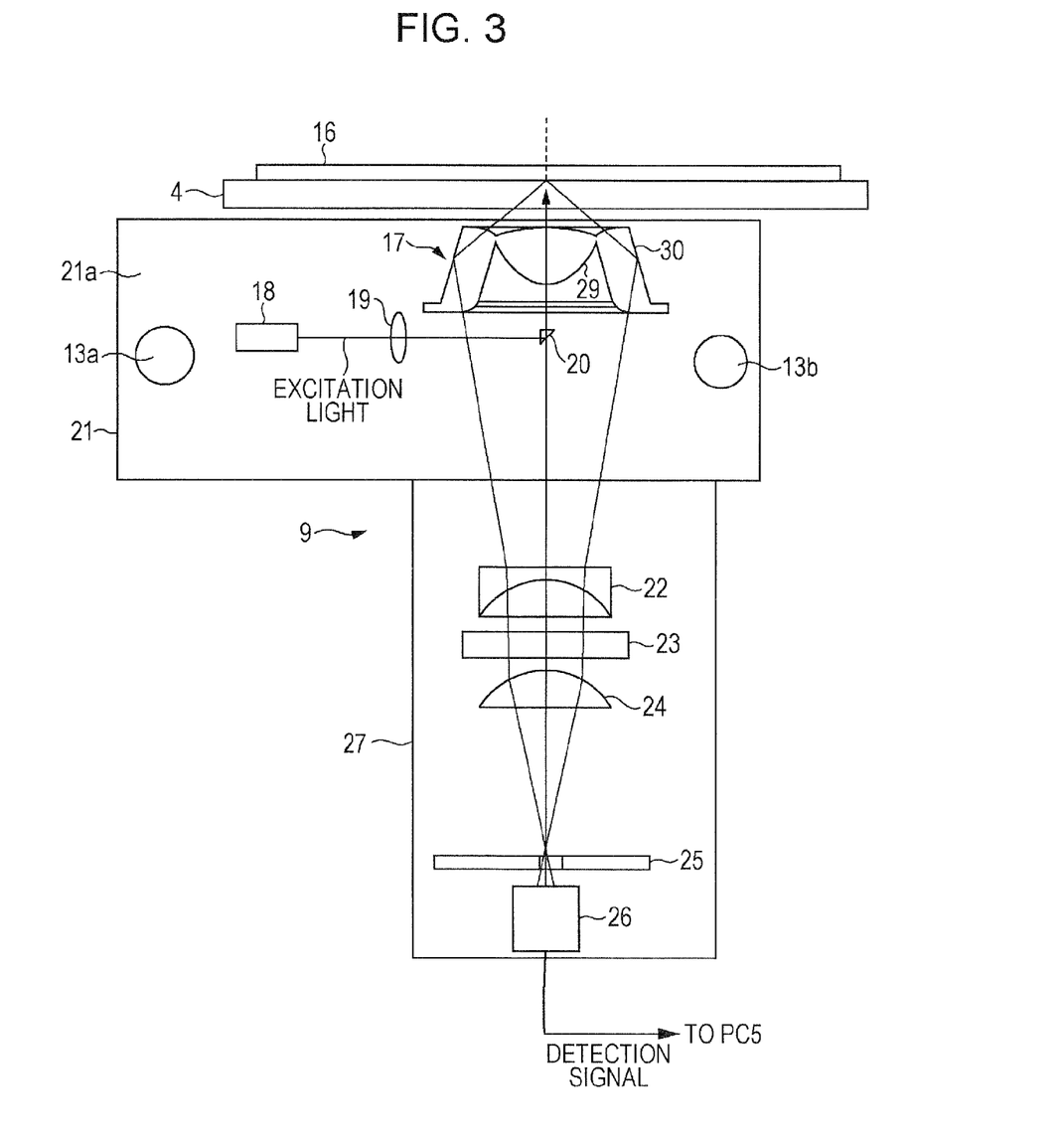
FIG. 3 is a cross-sectional view of a scanning module placed on a second stage in FIG. 2.

FIG. 3 is a longitudinal cross-sectional view illustrating a schematic configuration of the scanning module 9 placed on the second stage 8.

In FIG. 3, an objective lens 17 is disposed at the upper portion of the scanning module 9. The objective lens 17 is positioned in the vicinity of the sample stand (glass) 4 and concentrates fluorescence from the sample 16 set on the sample stand 4. A prism 20 is disposed at a location in which an optical axis of the objective lens 17 and an optical axis of a light source 18 of excitation light are orthogonal to each other. The prism 20 reflects excitation light such as a laser beam, which is emitted from the light source 18 and concentrated at a first lens 19 so as for the excitation light to be incident to the objective lens 17.

The excitation optical system is configured by the light source 18, the first lens 19, the prism 20, and the objective lens 17. The excitation optical system is fixed to and supported by a metal frame 21. Thus, a heat dissipation property of the light source 18 is improved and the excitation optical system has a structure in which thermal deformation is unlikely to occur. Accordingly, it is possible to concentrate the excitation light emitted from the light source 18 at one minute point on the sample 16 without shifting. Because variance at the one minute point on the sample 16 is small, the length of the prism 20 in a longitudinal direction (direction orthogonal to an optical axis of the first lens 19) becomes short, the width of the prism 20 in a direction orthogonal to the longitudinal direction becomes narrow, and thus the size of the prism 20 may be reduced.

In FIG. 3, a second lens 22, a wavelength filter 23, a third lens 24, and a pinhole 25 are disposed under the prism 20 on the optical axis of the objective lens 17 in order from a prism 20 side. The second lens 22 converts fluorescence from the sample 16 and concentrated by the objective lens 17 into collimated light. The wavelength filter 23 is used for cutting the excitation light. The third lens 24 concentrates fluorescence passing through the wavelength filter 23. The pinhole 25 cuts off stray light of the fluorescence passing through the third lens 24. A detector 26 is disposed under the pinhole 25 in the optical axis of the objective lens 17. The detector 26 includes the detection element that detects the fluorescence passing through the pinhole 25.

The detection optical system configured by the second lens 22, the wavelength filter 23, the third lens 24, the pinhole 25 and the detector 26 is fixed to and supported by a resin frame 27.

As described above, in FIG. 3, the diameter of fluorescence is large, and thus the second lens 22 and the third lens 24 with a large aperture are used in the detection optical system. In that case, if a frame for supporting the lenses 22 and 24 with a large aperture is formed of metal, the weight of the detection optical system increases. Thus, it is difficult for the scanning module 9 to perform high-speed scanning and a scanning time becomes long.

On the other hand, if the resin frame 27 is used as the frame for supporting the lenses 22 and 24 with a large aperture without any scheme for weight reduction, an optical axis of the detection optical system is shifted from a designed position by distortion of the frame 27, and thus it is impossible to obtain desired performance of the detection optical system.

In the embodiment, the optical axis of the detection optical system is set to a vertical direction and the resin frame 27 supporting the detection optical system is attached to be hung on a lower surface of the metal frame 21. In this manner, even when the resin frame 27 is used as the frame supporting the lenses 22 and 24 with large to achieve the weight reduction, deformation of the detection optical system is limited to occur in only optical axis direction, and thus it is possible to reduce variance of the optical axis by the weight of the detection optical system.

In the scanning module 9 having the above-described configuration, excitation light emitted from the light source 18 is converged in the first lens 19, reflected from the prism 20, passes through the objective lens 17 and the sample stand 4, and is concentrated at one point on the lower surface in the sample 16. In that case, the length of the prism 20 in the longitudinal direction (direction orthogonal to the optical axis of the first lens 19) becomes short and the width of the prism 20 in the direction orthogonal to the longitudinal direction becomes narrow. Thus, the excitation light from the light source 18 passes through only the vicinity of the optical axis of the objective lens 17 (excitation light transmission portion).

The fluorescence is emitted isotropically from a portion to which the excitation light is applied to the vicinity in the sample 16. A component of the emitted fluorescence passes through the objective lens 17, the second lens 22, the wavelength filter 23, the third lens 24, and the pinhole 25 and is detected by the detector 26. The component is transmitted by the sample stand 4 formed of glass and incident to the objective lens 17. Processes such as AD conversion by a built-in AD converter and the like are performed on a signal detected by the detector 26, and the processed signal is output to the PC 5. In this manner, distribution of fluorescence intensity at measurement points on the sample 16 is stored in an internal memory and the like.

As described above, the fluorescence passing through the objective lens 17 becomes convergent light and is guided in a direction of the second lens 22. The guided light is refracted by the second lens 22 so as to be substantially collimated light. The third lens 24 concentrates the fluorescence. The pinhole 25 is disposed to spatially cut off stray light. The wavelength filter 23 for cutting off the excitation light is disposed, for example, on a rotary folder and may be replaced with another wavelength filter 23a depending on a wavelength of the excitation light.

As illustrated in FIG. 3, a center portion including the optical axis in the objective lens 17 is formed to be a convex lens portion 29 that has a function of a general convex lens (deflection of light in only a case of refraction). Fluorescence having a small radiation angle among the fluorescence emitted from the sample 16 passes through a part of the convex lens portion 29 to the detector 26 and is concentrated.

The vicinity of the convex lens portion 29 in the objective lens 17 is formed to be a cylindrical object 30 which is open downwardly and has a truncated cone shape. Fluorescence which has a large radiation angle and does not enter the convex lens portion 29 among the fluorescence emitted from the sample 16 is incident from an upper end surface of the cylindrical object 30 into the cylindrical object 30. The incident fluorescence is reflected totally on a circumference surface of the cylindrical object 30, deflected to an optical axis side, and emitted from a lower end surface of the cylindrical object 30 to the detector 26.

In the above description, the fluorescence which has a large radiation angle and does not enter the convex lens portion 29 among the fluorescence emitted from the sample 16 is reflected totally on the circumference surface of the cylindrical object 30. Thus, it is possible to concentrate light having a large radiation angle, and it is impossible for the general convex lens to concentrate the light. Accordingly, it is possible to achieve high sensitivity of the detector 26.

The scanning device formed by, for example, a timing belt is connected to the metal frame 21. Two holes for inserting a guide shaft are formed on side surfaces 21a and 21a (only one side surface 21a appears in FIG. 3). The side surfaces 21a and 21a face each other in the metal frame 21. The two guide shafts 13a and 13b are inserted into the holes and disposed horizontally. Furthermore, the resin frame 27 supporting the detection optical system is attached to a lower surface of the metal frame 21 supporting the excitation optical system such that the optical axis of the objective lens 17 matches the optical axis of the detection optical system, and the resin frame 27 is hung in the vertical direction. As a result of this, the resin frame 27 has a reduced weight and the center of gravity is on a metal frame 21 side. Accordingly, it is possible to suppress distortion or vibration of the scanning module 9 occurring when the scanning device performs scanning.

A first scanning device of the second stage 8 and a second scanning device of the scanning module 9 will be described below. The first scanning device performs first scanning in the first scanning direction. The second scanning device performs second scanning in the second scanning direction.

Figure 4:
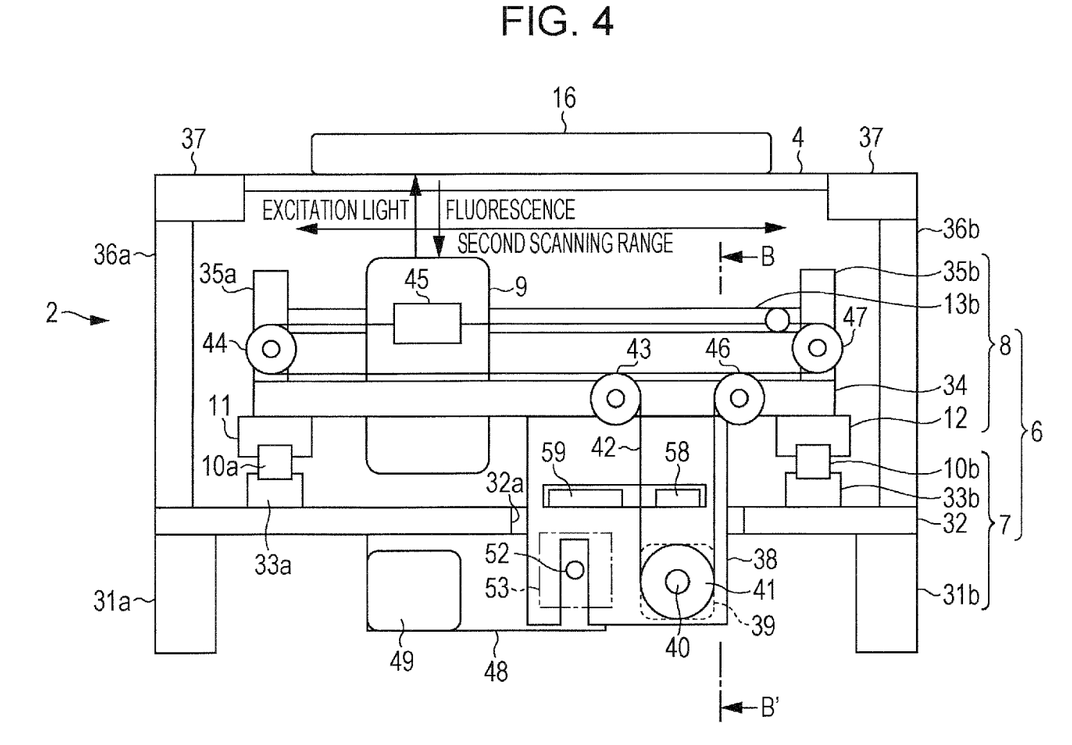
FIG. 4 is a longitudinal cross-sectional view taken in a second scanning direction of a main body illustrated in FIG. 1.

FIG. 4 is a longitudinal cross-sectional view of the main body 2 in the second scanning direction illustrated in FIG. 1. In FIG. 4, two supports 31a and 31b have a bar shape and a rectangular cross section. The supports 31a and 31b are disposed parallel to each other with a distance in the first scanning direction. A plate-shaped first plate 32 bridges the two supports 31a and 31b. The two guide rails 10a and 10b are placed on two pedestals 33a and 33b. The two guide rails 10a and 10b face each other with a constant distance and are arranged over the first plate 32 in the first scanning direction. In this manner, the first stage 7 is configured by the supports 31a and 31b, the first plate 32, the pedestals 33a and 33b, and the guide rails 10a and 10b.

The first guide member 11 is guided by the guide rail 10a. The first guide member 11 is installed on the guide rail 10a to be able to perform a reciprocating operation. The second guide member 12 is guided by the guide rail 10b. The second guide member 12 is installed on the guide rail 10b to be able to perform a reciprocating operation. A plate-shaped second plate 34 bridges the first guide member 11 and the second guide member 12.

Shaft attachment plates 35a and 35b are set up on both ends of the second plate 34 in the second scanning direction. The two guide shafts 13a and 13b facing each other with a constant distance are arranged between the two shaft attachment plates 35a and 35b. As described above, the guide shafts 13a and 13b are inserted into the holes for insertion which are disposed in the metal frame 21 of the scanning module 9. In this manner, the second stage 8 is configured by the first and the second guide members 11 and 12, the second plate 34, the shaft attachment plates 35a and 35b, and the guide shafts 13a and 13b.

In FIG. 2, for easily understandable description, the guide shafts 13a and 13b are illustrated to be attached directly to the first and the second guide members 11 and 12.

Side plates 36a and 36b are set up on both ends of the first plate 32 in the second scanning direction. The side plates 36a and 36b constitute an outer shell of the main body 2 illustrated in FIG. 1. A rectangular frame body 37 is placed on an upper end of the side plates 36a and 36b, and side plates (not illustrated) so that the outer shell of the main body 2 is formed. The side plates (not illustrated) are adjacent to the side plates 36a and 36b, constitute the outer shell of the main body 2, and face each other. The sample stand 4 formed of glass is fit into the frame body 37.

An upper end of a first motor attachment plate 38 is attached to a lower surface of the second plate 34. The first motor attachment plate 38 extends downwardly and is substantially rectangular. Substantially half of part of the first motor attachment plate 38 on a lower side thereof is inserted into a rectangular opening 32a disposed in the first plate 32 and protrudes toward a lower side of the first plate 32. A first motor 39 for the second scanning is attached to a back side in FIG. 4, that is, a lower side than the first plate 32 in the first motor attachment plate 38.

A driving shaft 40 of the first motor 39 penetrates the first motor attachment plate 38. A first pulley 41 is attached to a tip end of the driving shaft 40. A timing belt 42 is extended around the first pulley 41. One end side of the timing belt 42 based on the first pulley 41 passes through the opening 32a of the first plate 32, and then is extended around a first idler 43 and a second pulley 44. The first idler 43 is rotatably attached to an end surface of the second plate 34 on a front side in FIG. 4. The second pulley 44 is rotatably attached to an end surface of the shaft attachment plate 35a on the front side. The one end side of the timing belt 42 is attached to a belt attachment portion 45 which protrudes toward and is disposed on the front side of the scanning module 9. Another end side of the timing belt 42 based on the first pulley 41 passes through the opening 32a of the first plate 32, and then is extended around a second idler 46 and a third pulley 47 and is attached to the belt attachment portion 45 of the scanning module 9. The second idler 46 is rotatably attached to an end surface of the second plate 34 on the front side. The third pulley 47 is rotatably attached to an end surface of the shaft attachment plate 35a on the front side. In this manner, the first motor 39 is rotated forwardly and reversely, and thus the scanning module 9 is pulled by the timing belt 42 and performs the second scanning in the second scanning direction.

Figure 5:
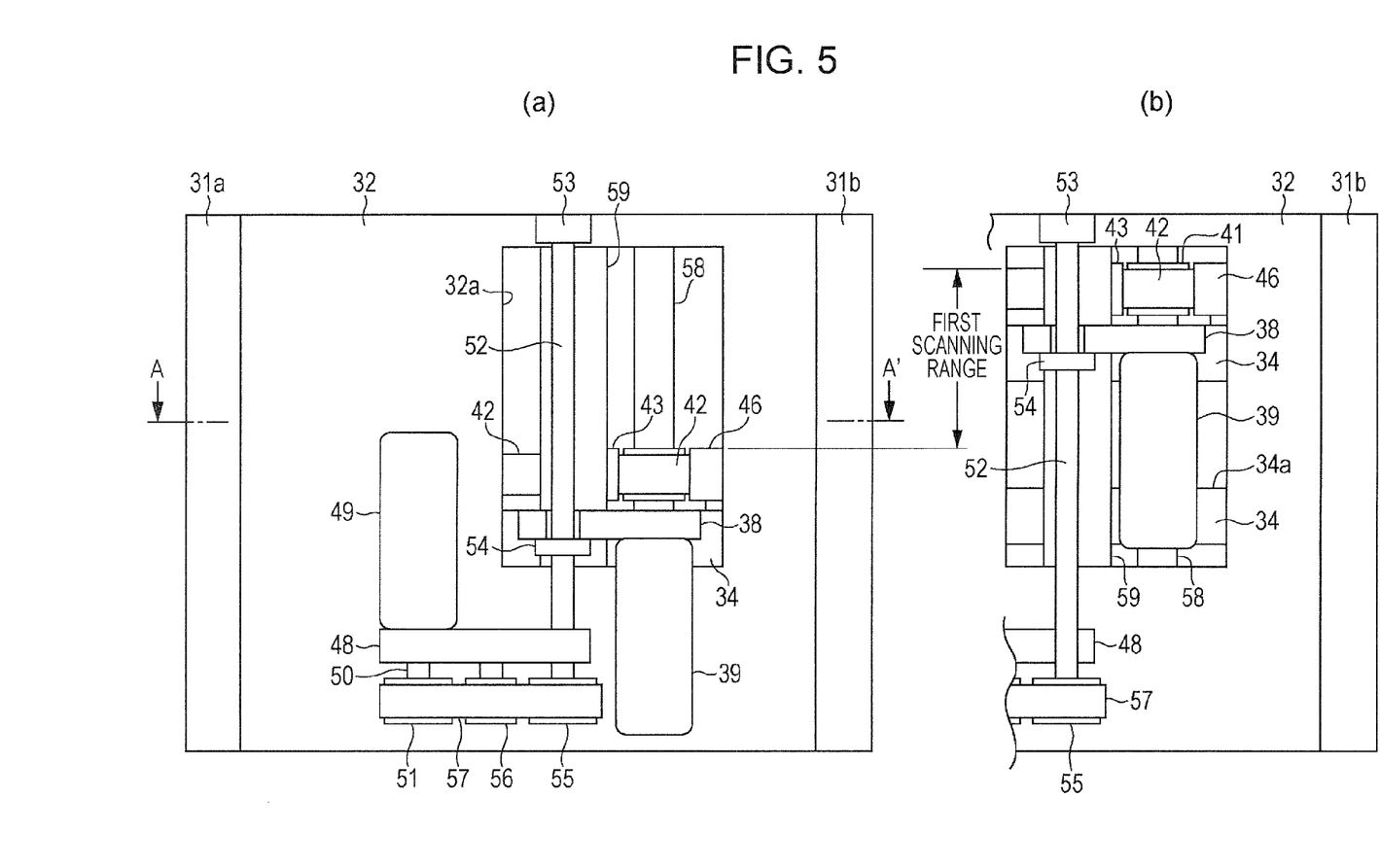
FIG. 5 is a bottom view of the main body illustrated in FIG. 1.

FIG. 5 is a bottom view corresponding to a view when the main body 2 illustrated in FIG. 4 is viewed from a lower side. FIG. 4 is a cross-sectional view taken along line A-A' indicated by arrows in FIG. 5.

In FIG. 5(a), the rectangular opening 32a of the first plate 32 is disposed unevenly on one side of the first plate 32. The first motor attachment plate 38 attached to the second plate 34 is inserted into the opening 32a. The first motor 39 is attached to a side of the first motor attachment plate 38 under the first plate 32. The first motor 39 is positioned on a further outer side than the opening 32a and faces the lower surface of the first plate 32.

As illustrated in FIG. 4 and FIG. 5(a), an upper end of a rectangular second motor attachment plate 48 is attached to another side with respect to the opening 32a on the lower surface of the first plate 32. A second motor 49 for the first scanning is attached to an opening 32a side of the second motor attachment plate 48. A driving shaft 50 of the second motor 49 penetrates the second motor attachment plate 48. A fourth pulley 51 is attached to a tip end of the driving shaft 50.

One end portion of a screw shaft 52 of a ball screw is inserted into and supported by the second motor attachment plate 48. Another end portion of the screw shaft 52 is supported by a bearing 53 disposed on one end portion side with respect to the opening 32a on a lower surface of the first plate 32. A nut 54 is screwed with the screw shaft 52 and constitutes the ball screw. The nut 54 is attached to the first motor attachment plate 38. A fifth pulley 55 is attached to the one end of the screw shaft 52. A third idler 56 is attached between the fourth pulley 51 and the fifth pulley 55. A timing belt 57 is extended around the fourth pulley 51 and the fifth pulley 55. In this manner, the second motor 49 is rotated forwardly and reversely, and thus the first motor attachment plate 38 performs reciprocating motion with the nut 54 in the first scanning direction. With this, the second plate 34 to which the first motor attachment plate 38 is attached and the scanning module 9 attached to the second plate 34 perform the first scanning.

FIG. 5(a) illustrates a state in which the first motor attachment plate 38 and the scanning module 9 are positioned at an end on a second motor attachment plate 48 in the first scanning direction. FIG. 5(b) illustrates a state in which the first motor attachment plate 38 and the scanning module 9 are positioned at an end opposite to the end in FIG. 5(a) in the first scanning direction.

A first cover 58 bridges movement locations of the first motor 39 in the opening 32a and a second cover 59 bridges movement locations of the screw shaft 52 along from the one side end to the other side end in an upper surface of the first plate 32. In this manner, heat radiated from the first motor 39 and the screw shaft 52 is blocked by the first and second covers 58 and 59 and is suppressed from being transferred from the opening 32a of the first plate 32 to a scanning module 9 side.

Figure 6:
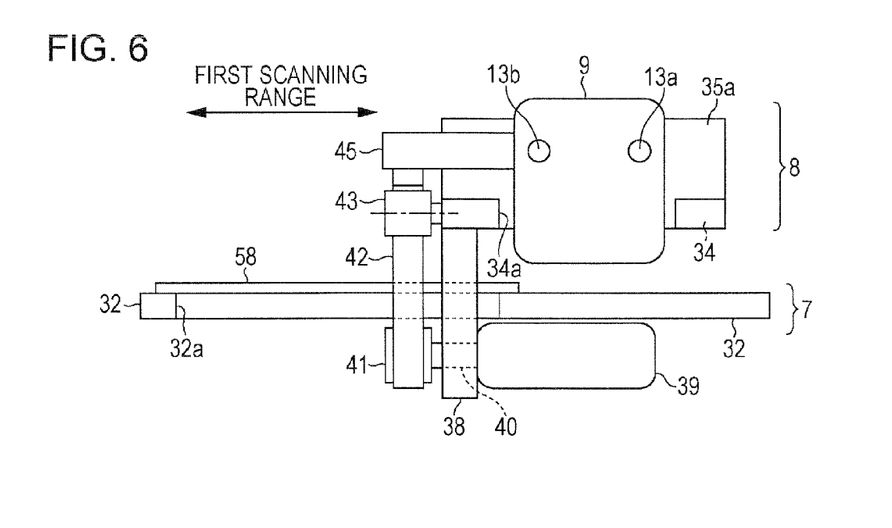
FIG. 6 is a cross-sectional view taken along line B-B' indicated by arrows in FIG. 4.

FIG. 6 is a cross-sectional view taken along line B-B' indicated by arrows in FIG. 4 and illustrates the second stage 8 and the second scanning device. As illustrated in FIG. 6, the first motor attachment plate 38 attached to the lower surface of the second plate 34 is inserted into the opening 32a in the first plate 32. The first motor 39 for the second scanning is attached to a side of the first motor attachment plate 38 under the first plate 32. The second plate 34 is disposed movably in the first scanning direction over the first plate 32. A lower side of the scanning module 9 is inserted into a rectangular opening 34a disposed in the second plate 34. The scanning module 9 causes the inside of the opening 34a to move in the second scanning direction.

As described above, in the embodiment, the first motor attachment plate 38 is inserted into the opening 32a disposed in the first plate 32. The first motor 39 is pulled down in a space on a lower side than the first plate 32. The timing belt 42 is guided from the space on a lower side than the first plate 32 to a space on an upper side so as to transfer a power of the first motor 39 to the scanning module 9 over the first plate 32. Furthermore, the second motor 49 for the first scanning is attached to the second motor attachment plate 48 attached to the lower surface of the first plate 32.

Accordingly, the scanning module 9 in which an optical system formed from the excitation optical system and the detection optical system is mounted is disposed over the first plate 34. The first and the second motors 39 and 49 being a heat source and a peripheral circuit for the motor (not illustrated) are disposed under the first plate 34. Thus, a configuration is formed in which it is difficult for the heat generated in the heat source to be transferred to the optical system. Accordingly, it is possible to reduce thermal deformation occurred in an optical member constituting the optical system by heat dissipation from the heat source. It is possible to prevent degradation of a fluorescence image obtained by the PC 5.

Furthermore, the opening 32a of the first plate 32 is disposed only in an area in which the first motor attachment plate 38 and the timing belt 42 move. Accordingly, it is possible to reduce the quantity of the heat which is transferred through the opening 32a and is transmitted from the heat source.

Furthermore, the first and the second covers 58 and 59 bridge the movement locations of the first motor 39 and disposition locations of the screw shaft 52 in the opening 32a. Accordingly, it is possible to block and reduce radiation heat from the first motor 39 and the screw shaft 52 in the first and the second covers 58 and 59, in which the radiation heat is transferred through the opening 32a.

Procedures in assembling of the main body 2 having the configuration will be described below.

Figure 7:
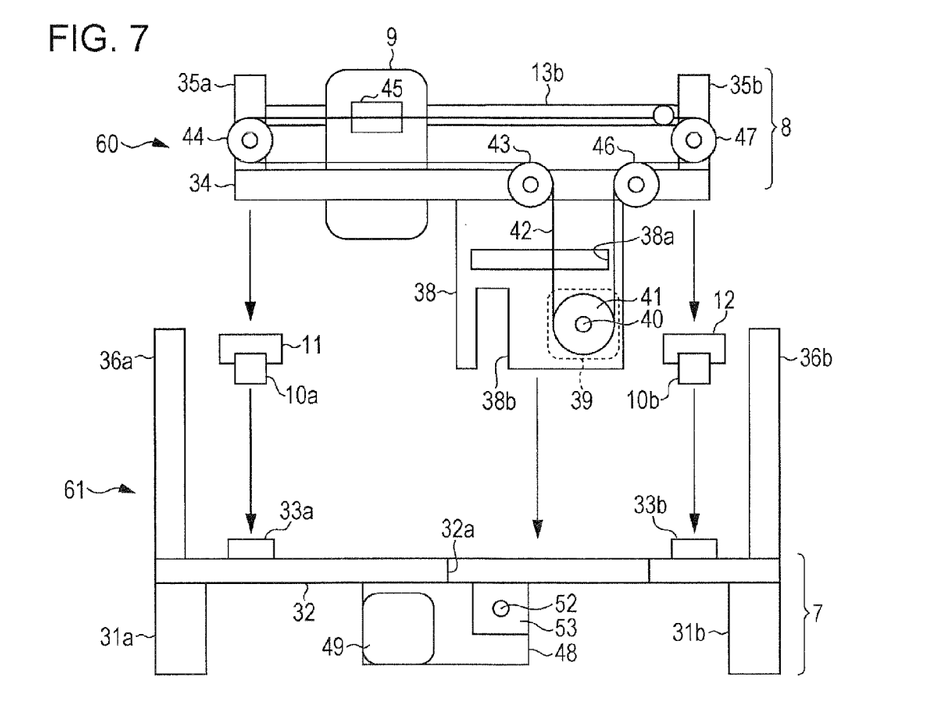
FIG. 7 is a front view illustrating a fitting method of a second scanning device to a first scanning device.
Figure 8:
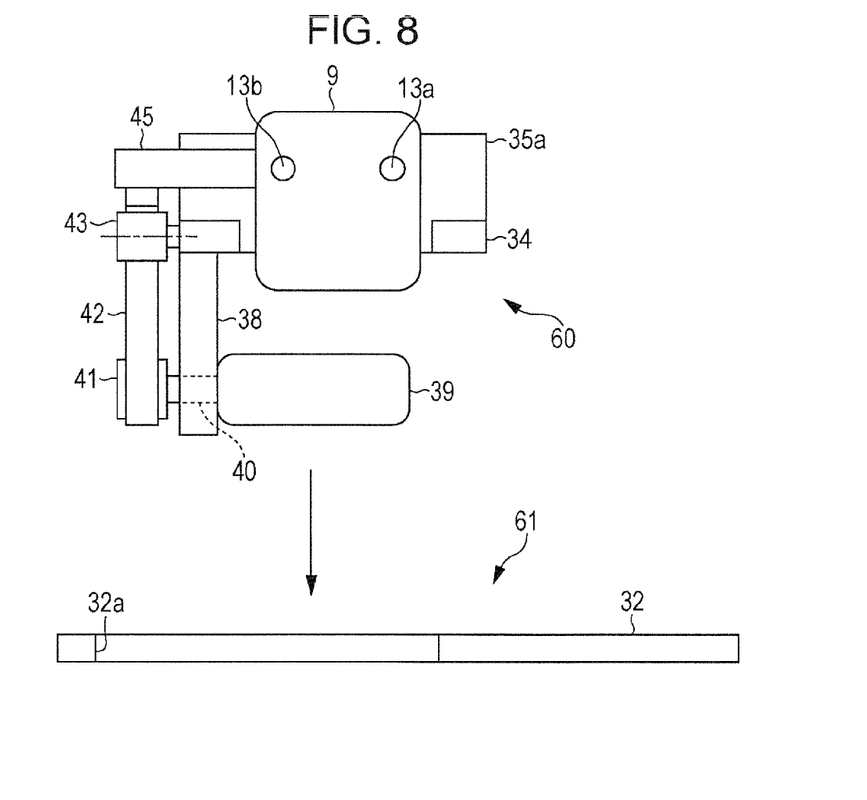
FIG. 8 is a cross-sectional view of FIG. 7.
Figure 9:
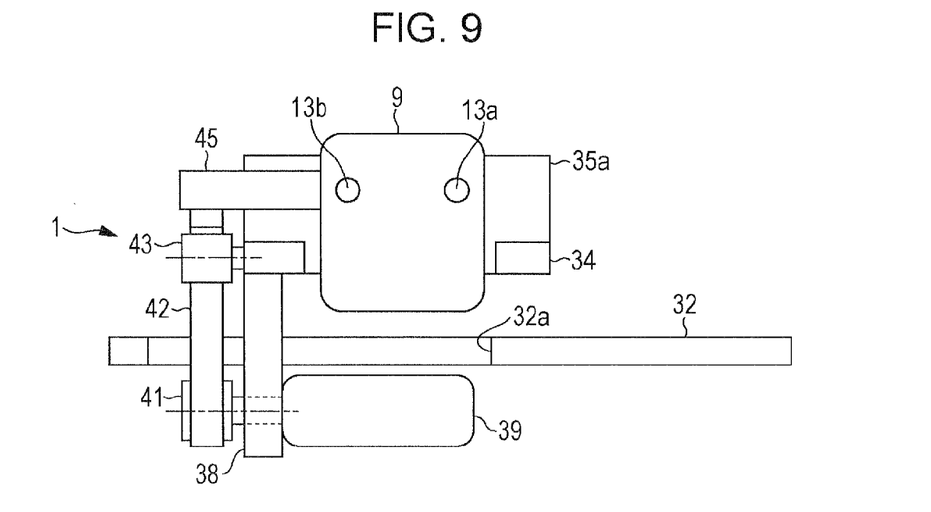
FIG. 9 is a cross-sectional view illustrating a state in which the second scanning device is fit to the first scanning device.
Figure 10:
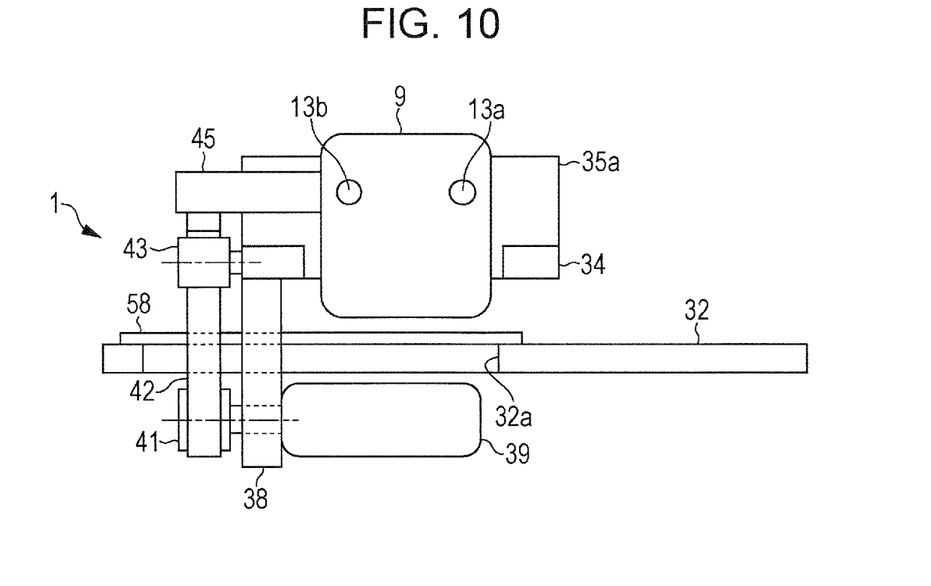
FIG. 10 is a cross-sectional view illustrating a state in which a first cover and a second cover are put.

FIG. 7 is a front view illustrating a fitting method of the second scanning device including the second stage 8 to the first scanning device including the first stage 7. FIG. 8 is a cross-sectional view of FIG. 7. FIG. 9 is a cross-sectional view illustrating a state in which the second scanning device is fit to the first scanning device. FIG. 10 is a cross-sectional view illustrating a state in which the first and the second covers 58 and 59 cross.

First, as illustrated in FIG. 7 and FIG. 8, the first plate 32 bridges the established supports 31a and 31b. Two pedestals 33a and 33b are established on the first plate 32. In this manner, the first stage 7 is formed. An upper end of the second motor attachment plate 48 is attached to the lower surface of the first plate 32. The second motor 49 and the screw shaft 52 are attached to the second motor attachment plate 48. The side plates 36a and 36b facing each other are set up on both ends of the first plate 32 in the second scanning direction. The side plates facing each other (not illustrated) are set up to be adjacent to the side plates 36a and 36b.

The shaft attachment plates 35a and 35b are set up on both ends of the second plate 34 in the second scanning direction. The two guide shafts 13a and 13b penetrating the scanning module 9 are disposed between the shaft attachment plates 35a and 35b. In this manner, the second stage 8 is formed. An upper end of the first motor attachment plate 38 is attached to a lower surface of the second plate 34. The first motor 39 is attached to the first motor attachment plate 38. The first pulley 41 is attached to the tip end of the driving shaft 40. A hole 38a having a slit shape is formed on the first motor attachment plate 38. The hole 38a is a hole into which the first and second covers 58 and 59 are inserted later. A slit 38b is formed on a lower portion of the first motor attachment plate 38 in the vertical direction. The slit 38b is a slit into which the screw shaft 52 is inserted when the second stage 8 is fit into the first stage 7 later.

Next, one end of the timing belt 42 is attached to the belt attachment portion 45 of the scanning module 9. The timing belt 42 is extended around the second pulley 44, the first idler 43, the first pulley 41, the second idler 46, and the third pulley 47. The other end thereof is attached to the belt attachment portion 45.

The second scanning device 60 as an example of the upper operation support section including the second stage 8 formed in this manner is inserted into the first scanning device 61 as an example of the lower operation support section including the first stage 7. The first motor attachment plate 38 on a second scanning device 60 side is inserted into the opening 32a on a first scanning device 61 side. The guide rails 10a and 10b and the first and second guide members 11 and 12 are interposed between the pedestals 33a and 33b on the first scanning device 61 side and the second plate 34 on the second scanning device 60 side, and the second scanning device 60 is fit to the first scanning device 61 in a direction indicated by arrows.

Consequently, as illustrated in FIG. 9, a fluorescence detection device 1 having a configuration in which the scanning module 9 in which the optical system is mounted is disposed over the first plate 32 and the first and second motors 39 and 49 being a heat source are disposed under the first plate 32, and a configuration in which the opening 32a of the first plate 32 is disposed in only the area in which the first motor attachment plate 38 and the timing belt 42 move in the first scanning direction is formed.

After that, as illustrated in FIG. 10, the first cover 58 bridges the movement locations of the first motor 39 in the opening 32a of the first plate 32. The second cover 59 bridges the disposition locations of the screw shaft 52. In this manner, the fluorescence detection device 1 which can block the radiation heat transferred from the first motor 39 and the screw shaft 52 through the opening 32a is formed.

Figure 11:
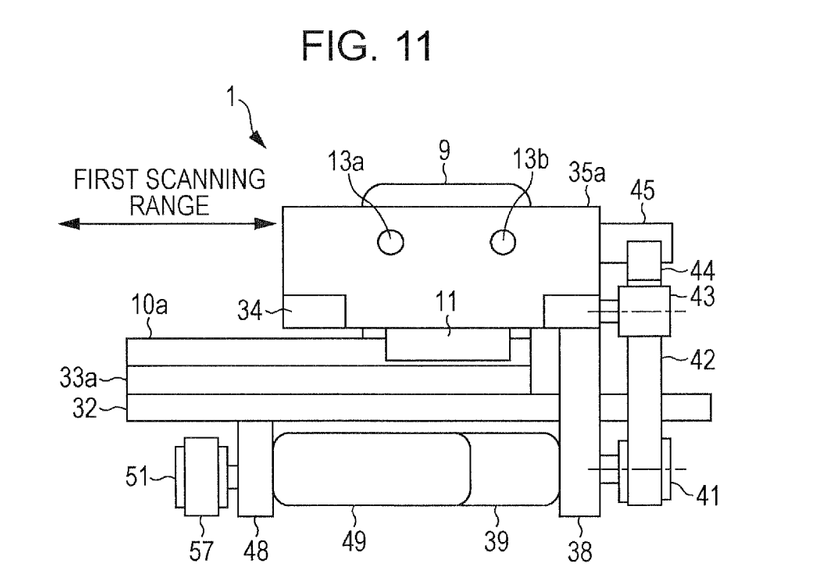
FIG. 11 is a view of the fluorescence detection device viewed from a side opposite to a side illustrated in FIG. 10.

FIG. 11 is a view of the fluorescence detection device 1 viewed from a side opposite to a side illustrated in FIG. 10.

In the above description, the embodiment includes the excitation optical system including the light source 18 which irradiates a measurement target (sample) with the excitation light, the detection optical system which detects fluorescence from the detection target to which the excitation light is applied, and the scanning module 9 which performs two-dimensional scanning in the first scanning direction and the second scanning direction vertical to the first scanning direction.

The upper operation support section which supports the scanning module 9 to perform a reciprocating operation along a plane direction of the first plate 32 which is set as an example of the reference stand and has a plate shape and the opening 32a in the second scanning direction, and includes the timing belt 42 and the first motor 39 as an example of the belt driving section is included. The lower operation support section which is disposed over the first plate 32, supports the upper operation support section to perform a reciprocating operation along a plane direction of the first plate 32 in the first scanning direction, and includes the pedestals 33a and 33b and the guide rails 10a and 10b is included.

In the configuration, the timing belt 42 of the upper operation support section is pulled down from a scanning module 9 side to a side opposite to the a scanning module 9 side through the opening 32a of the first plate 32 by the first motor attachment plate 38 as an example of the belt pulling-down section. The first motor 39 attached to the side opposite to the scanning module 9 side in the first motor attachment plate 38 rotation-drives the timing belt 42.

In this manner, according to the embodiment, the excitation optical system including the light source 18 which irradiates a measurement target with the excitation light, and the detection optical system which detects fluorescence from the detection target are stored in the one scanning module 9. Thus, it is possible for scanning module 9 to perform two-dimensional scanning by the lower operation support section and the upper operation support section. Accordingly, the length of an optical path from the light source 18 to the measurement target and the length of an optical path from the measurement target to the detection optical system become short and the lengths of the optical paths are not changed when two-dimensional scanning is performed.

Furthermore, the first motor 39 being a heat source is disposed on the side opposite to the scanning module 9 side using the first plate 32 as a boundary. Accordingly, it is possible to reduce heat transferred from the first motor 39 to the scanning module 9. As a result, it is possible to prevent accuracy of fluorescence detection from degrading due to thermal distortion of a detection optical system in the scanning module 9.

The first plate 32 is configured to have high rigidity and mass such that the first plate 32 has appropriate stability in vibration or impact as well as heat. The upper operation support section is directly disposed on the first plate 32 having appropriate stability in heat, vibration, and impact or is indirectly disposed on the first plate 32 through another member. Consequently, the upper operation support section has a stable structure from the vibration of the first motor 39.

As described above, the first motor 39 is disposed on the side opposite to the scanning module 9 side with respect to the first plate 32. Accordingly, it is unnecessary to provide a space for disposition of the first motor 39 on a scanning module 9 side of the first plate 32. Accordingly, it is possible to reduce the height from the stable first plate 32 to the optical detection section and it is possible to improve stability in operating of the optical detection section and to reduce the size of the entirety of the fluorescence detection device 1.

In the embodiment, the first motor 39 of the upper operation support section and the timing belt 42 is configured to perform a reciprocating operation in the first scanning direction by the lower operation support section in a state where the first motor 39 and the timing belt 42 are supported to hold relative positions by the first pulley 41, the first idler 43, the second pulley 44, the second idler 46, and the third pulley 47 as an example of the belt holding portion. Accordingly, it is possible for the lower operation support section to support the entirety of the upper operation support section including the first motor 39 such that the entirety of the upper operation support section moves integrally. As a result, movement in the first scanning direction and movement in the second scanning direction may not be affected by each other and may be completely independent from each other and thus it is possible for the scanning module 9 to easily perform the two-dimensional scanning.

Here, the independence of the movement means that a position relationship between the first motor 39 of the upper operation support section and the scanning module 9 is not changed by moving of the lower operation support section. For example, because the position relationship between the first motor 39 and the scanning module 9 is not changed in a case of movement in the first scanning direction, the length of the timing belt 42 necessary for transferring a driving force is not changed and tension of the timing belt 42 is not changed. Thus, an adjustment mechanism or the like for the tension of the timing belt 42 is not necessary. That is, it is possible to constitute the operation support section in the first scanning direction and the second scanning direction as a simple one axis direction operation mechanism.

In the embodiment, as illustrated in FIG. 5, the opening 32a of the first plate 32 is long in the first scanning direction by the lower operation support section.

It is necessary to reduce an area of the opening 32a of the first plate 32 as much as possible so as to reduce heat transfer from the first motor 39 to the scanning module 9. Accordingly, it is desired to set the opening 32a to the minimum area to match movement of the first motor attachment plate 38 as the belt pulling-down section in the first scanning direction.

A transmission operation of the timing belt 42 is performed in movement in the second scanning direction, but the position of the first motor attachment plate 38 in the second scanning direction is not changed. On the other hand, because the entirety of the upper operation support section moves integrally in moving in the first scanning direction, the first motor attachment plate 38 moves in the first scanning direction. That is, a movement range of the first motor attachment plate 38 is set to only the first scanning direction. Thus, the opening 32a is desired to be long in the first scanning direction so as to reduce the area of the opening 32a to the minimum.

In the embodiment, the lower operation support section is configured to include a guide section, the second motor 49, the fourth pulley 51, the third idler 56, the fifth pulley 55, and the timing belt 57. The guide section includes the pedestals 33a and 33b and the guide rails 10a and 10b. The pedestals 33a and 33b and the guide rails 10a and 10b guide the upper operation support section including the first motor 39 and the timing belt 42 in the first scanning direction. The second motor 49, the fourth pulley 51, the third idler 56, the fifth pulley 55, and the timing belt 57 are set as an example of the driving section driving the entirety of the upper operation support section in the first scanning direction.

In this manner, the second motor 49 is positioned on the side opposite to the scanning module 9 with respect to the first plate 32 and is disposed to transfer a driving force to the first motor attachment plate 38 through the screw shaft 52 and the nut 54.

Accordingly, not only the first motor 39 of the upper operation support section but also the second motor 49 is disposed on the side opposite to the scanning module 9 of the first plate 32, and thus it is possible to prevent heat from both of the first motor 39 and the second motor 49 from being transferred to the scanning module 9.

In the embodiment, the opening 32a of the first plate 32 is blocked by the first cover 58 and the second cover 59 avoiding a portion where the timing belt 57 and a part of the first motor attachment plate 38 pass through when the scanning module 9 moves two-dimensionally. Accordingly, it is possible to further reduce the opening area of the opening 32a and to further reduce heat transfer from the first motor 39, the second motor 49, and the screw shaft 52 to the scanning module 9.

REFERENCE SIGNS LIST

1 fluorescence detection device,
4 sample stand,
5 PC,
6 scanning stage,
7 first stage,
8 second stage,
9 scanning module,
11 and 12 guide member,
13a and 13b guide shaft,
16 sample,
17 objective lens,
18 light source,
26 detector,
32 first plate,
34 second plate,
35a and 35b shaft attachment plate,
38 first motor attachment plate,
39 first motor,
41, 44, 47, 51, and 55 pulley,
42 and 57 timing belt,
43, 46, and 56 idler,
45 belt attachment portion,
48 second motor attachment plate,
49 second motor,
52 screw shaft,
53 bearing,
54 nut,
58 and 59 cover,
60 second scanning device,
61 first scanning device.

The invention claimed is:
1. A fluorescence detection device comprising:
a reference stand which has a plate shape and an opening;
a scanning module that includes a light source which emits excitation light for excitation of fluorescence and a detection optical system which detects fluorescence emitted from a detection target based on the irradiation of the excitation light, and scans two-dimensionally in a first scanning direction and a second scanning direction substantially orthogonal to the first scanning direction;

an upper operation support section which supports the scanning module to allow the scanning module to perform a reciprocating operation in the second scanning direction and in a plane direction of the reference stand; and a lower operation support section which is disposed on the reference stand and supports the upper operation support section to allow the upper operation support section to perform a reciprocating operation in the first scanning direction and in a plane direction of the reference stand, wherein the upper operation support section includes:
- a belt which causes the scanning module to perform a reciprocating operation in the second scanning direction,
- a belt driving section which drives the belt, and
- a belt pulling-down section which causes the belt to pass through the opening of the reference stand and to be pulled down from a scanning module side to a side opposite to the scanning module side, the belt driving section is positioned on the side opposite to the scanning module with respect to a surface of the reference stand and disposed in the belt pulling-down section, the opening extends farther in the first scanning direction than in the second scanning direction, and the belt pulling-down section moves laterally within the opening in the scanning direction.

2. The fluorescence detection device according to claim 1, wherein the upper operation support section includes belt holding portions which hold a relative position between the belt and the belt driving section to be a predefined position, and the upper operation support section is able to perform the reciprocating operation in the first scanning direction in a state where the relative position between the belt and the belt driving section is held to be the predefined position by the belt holding portions.

3. The fluorescence detection device according to claim 1, wherein the lower operation support section includes guide members which guide the upper operation support section in the first scanning direction, and driving sections which drive the entirety of the upper operation support section in the first scanning direction, and wherein the driving sections are positioned on the side opposite to the scanning module with respect to the surface of the reference stand and are disposed to transfer a driving force to the belt pulling-down section.

4. The fluorescence detection device according to claim 1, further comprising:

covers which cover the opening of the reference stand such that the belt and the belt pulling-down section are movable when the scanning module performs two-dimensional scanning.

5. The fluorescence detection device according to claim 1, wherein the detection target is loaded on a light transmissive sample stand, the scanning module is disposed to face a side of the sample stand opposite to a side of the sample stand on which the detection target is loaded, and the scanning module detects fluorescence emitted from the detection target through the sample stand while performing the two-dimensional scanning along the sample stand.

\* \* \* \* \*